United States Patent
Mehta et al.

(10) Patent No.: US 7,692,162 B2
(45) Date of Patent: Apr. 6, 2010

(54) IMAGING OF TWO-DIMENSIONAL ARRAYS

(75) Inventors: Suresh N. Mehta, Pleasanton, CA (US); Neeraj Bhatt, Fremont, CA (US); Kevin A. McDonald, Novato, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 251 days.

(21) Appl. No.: 11/956,004

(22) Filed: Dec. 13, 2007

(65) Prior Publication Data

US 2008/0149855 A1   Jun. 26, 2008

Related U.S. Application Data

(60) Provisional application No. 60/871,369, filed on Dec. 21, 2006.

(51) Int. Cl.
*G01N 21/17* (2006.01)
*G01N 21/25* (2006.01)
*G01N 21/62* (2006.01)

(52) U.S. Cl. ............... 250/491.1; 250/522.1; 204/612; 356/417; 356/326; 422/82.05

(58) Field of Classification Search ............. 250/491.1, 250/522.1; 204/612; 356/417, 326; 422/82.05
See application file for complete search history.

(56) References Cited

U.S. PATENT DOCUMENTS

| | | | |
|---|---|---|---|
| 4,960,999 A | 10/1990 | McKean et al. | |
| 5,141,609 A | 8/1992 | Sweedler et al. | |
| 6,512,577 B1 * | 1/2003 | Ozanich | ................. 356/73 |
| 6,649,416 B1 * | 11/2003 | Kauer et al. | ............. 436/164 |
| 6,856,390 B2 | 2/2005 | Nordman et al. | |
| 7,002,688 B2 * | 2/2006 | Aravanis et al. | ............ 356/417 |
| 7,076,394 B2 | 7/2006 | Ikeda | |
| 2003/0030804 A1 | 2/2003 | Nordman et al. | |
| 2003/0048933 A1 | 3/2003 | Brown et al. | |
| 2003/0139886 A1 | 7/2003 | Bodzin et al. | |
| 2004/0197793 A1 | 10/2004 | Hassibi et al. | |
| 2004/0263829 A1 | 12/2004 | Ikeda | |
| 2005/0036142 A1 | 2/2005 | Oldham et al. | |
| 2005/0213093 A1 | 9/2005 | Nordman et al. | |
| 2005/0240106 A1 | 10/2005 | Oravecz et al. | |
| 2006/0231400 A1 | 10/2006 | Inaba et al. | |

FOREIGN PATENT DOCUMENTS

| CA | 2453390 A1 | 2/2003 |
|---|---|---|
| WO | WO 03/0010524 A1 | 2/2003 |

* cited by examiner

*Primary Examiner*—Nikita Wells
(74) *Attorney, Agent, or Firm*—Townsend and Townsend and Crew LLP

(57) ABSTRACT

Images of two-dimensional chromatograms or other sample arrays are formed on a scanning instrument that utilizes a line of illumination light that sweeps the length of the array either by moving across the array or by the array moving relative to the light, in either case scanning the entire two-dimensional array with a unidirectional pass of the moving component. The use of a CCD equipped with time delay integration allows the instrument to form an enhanced image.

26 Claims, 2 Drawing Sheets

IMAGING OF TWO-DIMENSIONAL ARRAYS

CROSS-REFERENCE TO RELATED APPLICATION

This application claims the benefit of U.S. Provisional Patent Application No. 60/871,369, filed Dec. 21, 2006, the contents of which are incorporated herein by reference in their entirety.

BACKGROUND OF THE INVENTION

Clinical and research investigations in the various fields of biotechnology frequently involve the identification of the components of samples of biological mixtures, the components ranging from whole organisms to fragments of nucleic acids and proteins. The component species of a mixture are identified by any of a variety of separation procedures, prominent among which are electrophoresis, size exclusion chromatography, and isoelectric focusing. The sample is typically dissolved or suspended in an aqueous buffer solution, and the medium on which the separation is performed is typically a porous substrate such as a polyacrylamide or agarose gel. Depending on the experiment being performed, the sample either remains in the gel or is transferred to the surface of a membranous support, commonly known as a "blot," to allow greater accessibility. Since the separated species are often undetectable by themselves, they are associated for detection purposes with detectable moieties such as light-absorptive, radioactive, luminescent, or fluorescent reporter moieties. These reporter moieties are either covalently bound to the species prior to the separation or applied after the separation as general affinity stains or as biologically based molecule-specific probes. Procedures that include the attachment of reporter moieties to separated species are variously termed "Southern," "Northern," and "Western" blotting.

For chromatographically separated species, whether the separation has been performed in either one dimension or two dimensions, detection methods of choice have historically been those that generate an image of the array of separated species. Such images have traditionally been recorded on x-ray film or on photographic negatives and prints. Digital imaging has since been developed and has grown in popularity in recent years as digital technology has improved and become more accessible to the scientific community. At present, the most common imaging techniques are those involving the use of charge coupled devices (CCDs). CCDs are particularly well suited to the imaging of chromatographic arrays because of the sensitivity of CCDs in both the visible and near-infrared spectra, where the most biological sample detections occur.

A digital imaging instrument generally combines a CCD camera with a light source(s) to illuminate the biological sample, with both the CCD camera and the light source(s) retained in an enclosure that is sealed against ambient light. Depending on its design, the instrument may contain or implement light sources that emit excitation light at specific wavelength bands and yet include a range of emission filters that allow the detection of specific reporter moieties to be optimized by selecting the most appropriate filter.

SUMMARY OF THE INVENTION

The present invention resides in an integrated imaging platform for biological samples that includes an area CCD camera with time delay integration readout, a light source that produces an excitation beam in the form of a line of light, and a sample holder with a dedicated sample area, with either the light source or the sample holder operating as a motorized component that moves in a linear direction. Over the course of travel of the motorized component, the entire area of a two-dimensional chromatogram or other sample array on the sample area, or a two-dimensional section of interest within the sample array, is exposed to the line of light. In certain embodiments the apparatus also includes multiple emission filters, and in all cases, movement of the motorized component and the selection of the appropriate filters if included is coordinated through control software in a computer. The light source is configured such that the line of light spans the width of the sample area, and as the motorized component moves, whether it be the light source or the sample holder, the line of light sweeps the full length of the sample area and hence the sample array. Accordingly, there is no limitation on the length of a sample array that can be imaged by the system of this invention. The images acquired by this invention can be formed by any of a variety of detection methodologies. Examples of such methodologies are fluorescence, colorimetric measurements, chemiluminescence, and densitometry. Preferred embodiments of the invention also offer the capability of capturing a full two-dimensional image from a stationary sample, using the same detector that is used for the longitudinal sweep of the line of light across the sample area.

DETAILED DESCRIPTION OF THE INVENTION AND PREFERRED EMBODIMENTS

While the features defining this invention are capable of implementation in a variety of constructions, the invention as a whole will best be understood by a detailed examination of a specific embodiment. One such embodiment is shown in the attached figures.

Figure 1:
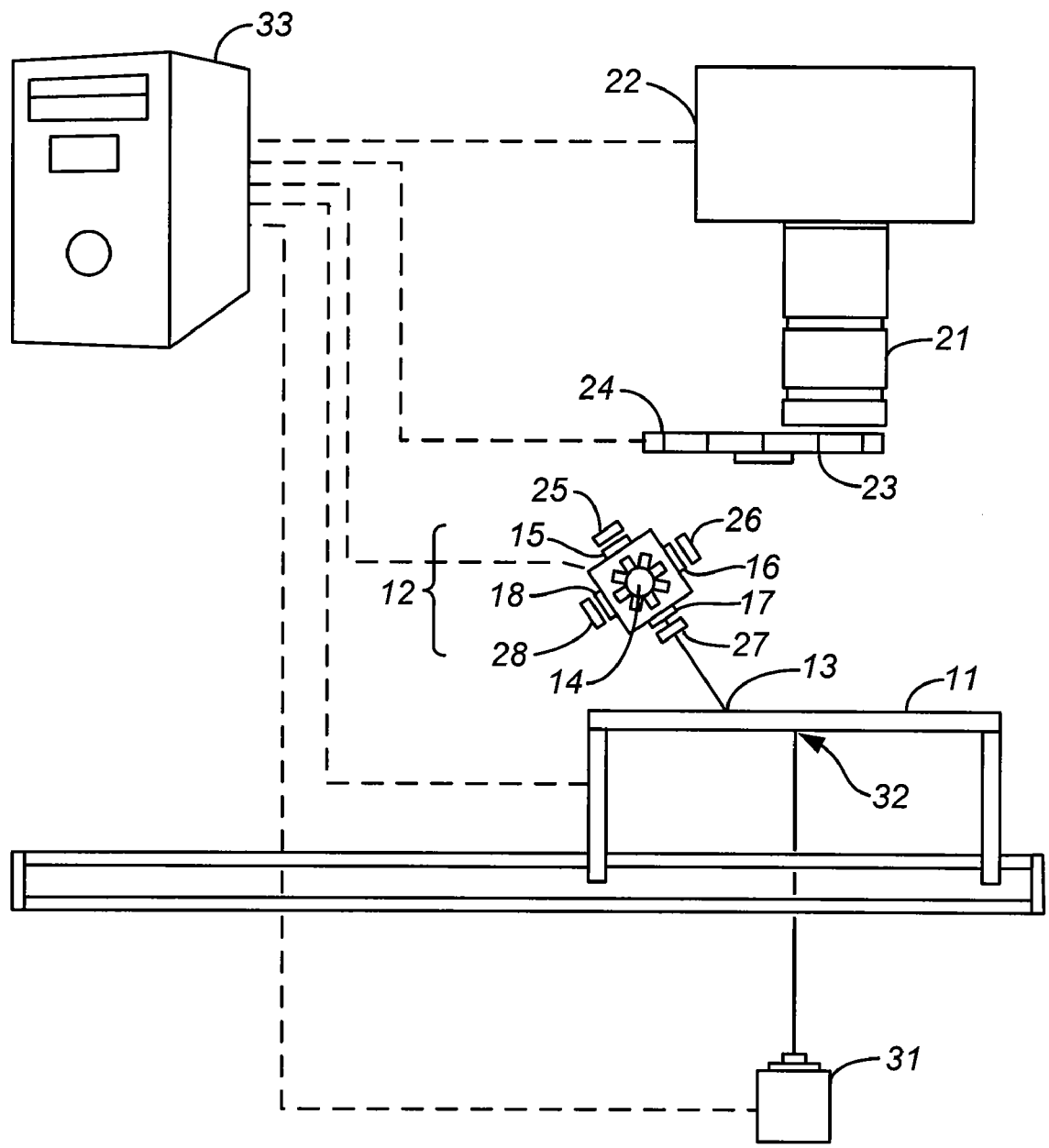
FIG. 1 is a diagram of an imaging system of the present invention.

In this embodiment, the sample, which can be a gel, a blot, or a phosphor screen, is placed on a platen. In FIG. 1, the platen, serving as a sample tray, is located on a sample holder or stage 11 that moves from left to right (in the view shown in the figure) at a precisely controlled speed. A source 12 of excitation light is positioned above the sample (a configuration referred to as epi-illumination). The excitation light is a line of light 13, i.e., a straight line of light of uniform or substantially uniform intensity, oriented to be perpendicular to the direction of movement of the stage and to span the width of the sample tray.

The sample stage 11 can be moved by any conventional linear motion drive. An example is a lead screw that is driven by a stepper motor or by a DC motor with an encoder to detect the position of the stage as it moves and regulates the movement in a precise manner. The stage itself can be mounted on a slide or guide rods with bushings. Other examples of the drive and the stage mounting will be readily apparent to those skilled in the art, such as a motorized rack and pinion drive. In embodiments of the invention in which the light source moves rather than the sample stage, the same types of linear motion drives can be used.

Figure 2:
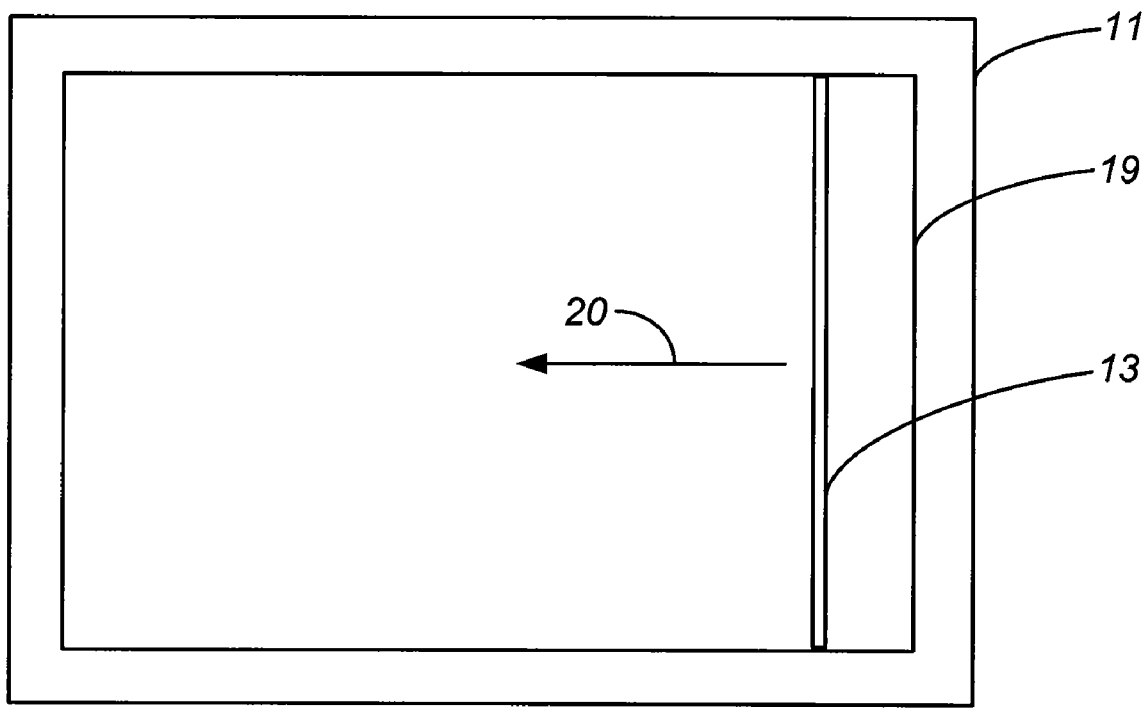
FIG. 2 is a plan view of the sample holder of the system of FIG. 1.

FIG. 2 is a top view of the sample stage 11, showing the sample area 19 on the surface of the stage. The line of light 13 spans the width of the sample area 19, and moves in the direction indicated by the arrow 20 to sweep the full length of the sample area.

The line of light can be formed by a series of LEDs in a closely spaced linear array. The spacing between adjacent LEDs may, for example, be 1 mm or a distance on the order of 1 mm. When LEDs are used, the light emitted by the LEDs can be collimated by a lens and is incident on the stage as a narrow swath of light across the sample. The configuration and placement of the LEDs are chosen to produce bright and substantially uniform illumination along the length of the line of light. The LEDs are also chosen such that the wavelength band of the line of light is nominally in the desired excitation band for the reporter moieties in the sample. Preferably as well, an interference optical band pass filter is placed between the line of light and the sample to remove essentially all traces of light that may also be emitted by the LED but are outside the desired excitation band. The interference filter allows the light in the desired band to pass by absorbing the light outside the band.

For reporter moieties that produce fluorescence signals, i.e., fluorescence labels or stains, one set of wavelengths for excitation and emission may be optimal for one label or stain and other sets may be optimal for other labels or stains. To accommodate different labels or stains, the instrument can be designed to allow a selection among different wavelengths for excitation and a selection among different emission filters to detect emissions at different wavelengths. One means of achieving a selection of wavelengths for excitation is by mounting two or more light sources on a rotating turret 14. The number of wavelengths that can be made available in this manner can vary widely. In the embodiment shown in the figure, four different light sources 15, 16, 17, 18 are mounted to the turret 14, each emitting a line of light at a different wavelength and each coupled with an appropriate excitation band pass filter 25, 26, 27, 28. In other embodiments, the turret can accommodate five, six, or more light sources producing lines of light of different wavelengths. These embodiments allow the system to assemble images of a sample with multi-colored reporter moieties and to superimpose these images for further data analysis. Another means of producing lines of light of different wavelengths is by mounting the light sources on a slide and by moving the slide to place the light with the wavelength of choice for a particular application in position for proper alignment with the sample stage 11. An alternative light source is a laser, which can be formed into a line of light by suitable optics whose choice and configuration will be apparent to those skilled in the art. Multiple lasers emitting at different wavelengths can likewise be mounted on a turret. Still other light sources, known to those skilled in the art, that can produce or be formed into a line of light, can be used.

When the turret is formed with a hollow core, it can be continuously purged with a coolant to remove the heat generated by the light source(s). A stream of air for example can serve as the coolant. The turret thus acts as an effective heat sink.

The fluorescent light emitted by the sample as a result of the excitation is collected by a lens 21 which directs the light to the CCD chip of a camera 22 where the light forms an image of the chromatogram or other sample array. Before reaching the detector, however, the emitted light passes through an emission filter 23. A motorized filter wheel 24 allows the selection of the appropriate filter for a given excitation light source. The filter also blocks any scattered excitation light.

As the stage 11 travels, the line of excitation light 13 travels over the sample that is supported by the stage, and the CCD camera 22 forms an image of the emitted light. Imaging is achieved by conventional means, including the generation of electrons in pixels by the collection of photons from the sample emissions. The electrons thus generated are continuously transferred across the CCD from one column of pixels to the next in the direction of travel. The rate of clocking of each column of pixels on the CCD is proportional to, and synchronized with, the stage speed, such that once a given point on the sample traverses the line of light, the fluorescence at the point continues to be emitted and focuses on the conjugate pixel elements that continue to generate electrons. As the image of the traveling point shifts from one column of pixels to the next, the generated electrons are transferred between the pixel columns at exactly the same rate. The electrons are thus accumulated in the pixel array before the charge is recorded, in a process known as time delay integration. In this manner, the collection of electrons from a sample point is enhanced.

Descriptions of time delay integration are found in the prior art. Examples of literature containing such descriptions are:

Sweedler et al. (The Trustees of the Leland Stanford Junior University), U.S. Pat. No. 5,141,609, issued Aug. 25, 1992. The system described in this patent includes a CCD in time delay integration mode and is designed for scanning electrophoresis capillaries rather than two-dimensional media such as gels and membranes.

Nordman et al. (Applera Corporation) U.S. Pat. No. 6,856, 390 B2, issued Feb. 15, 2005. The apparatus described in this patent contains a linear array of detectors operating in time delay integration mode for the analysis of liquid samples in capillaries and channels.

Ikeda (Kabushiki Kaisha Toshiba), U.S. Pat. No. 7,076,394 B2, issued Jul. 11, 2006. This patent describes the scanning of document and photographs with a time delay integration sensor to detect either reflected light or transmitted light.

Applera Corporation, International Application Publication Number WO 03/010524 A1, international publication date Feb. 6, 2003. The system described in this patent application is used on samples held in capillaries or channels, and operates by simultaneously illuminating an area of the sample with multiple illumination wavelengths and capturing the emitted signals with an area detector in time delay integration mode.

Although various detection methodologies can be used in the practice of this invention as noted above, the invention is particularly useful on samples that emit fluorescence, where the typical excitation wavelengths are nominally 365, 405, 470, 490, 530, 630, 660, and 780 nm. Additional wavelengths can also be used, however, such as those produced by UV LEDs with emissions below 365 nm. As noted above, the presently preferred configuration is one that allows a selection among four different wavelengths.

The emission filter wheel 24 in the embodiment shown in the figure can accommodate up to six filters to correspond with the emission wavelengths. The selection can be performed automatically. While the filter wheel is in front of the lens 21 in the configuration shown in the figure, the wheel can also be located within the camera between the lens 21 and the CCD chip in the camera 22.

While the descriptions above address the use of a full frame CCD camera operating in time delay integration mode for enhancing the signal strength in fluorescence imaging, a similar enhancement in signal strength is achievable with colorimetric imaging, including both chemiluminescent imaging and reflective imaging.

In alternative embodiments of the present invention, trans-illumination is used rather than epi-illumination. Trans-illumination is achieved in FIG. 1 by a light source 31 positioned below the sample stage. This light source, like the epi-illumination light source 12, produces a line of light 32, but one that passes through the sample stage 11 from underneath rather than striking the sample stage from above. One example of a mode of detection that can effectively make use of trans-illumination is densitometry, using light absorption measurements. Non-opaque samples, such as Coomassie-stained or silver-stained gels, whose components absorb light in the visible spectrum, are examples of samples suitable for this type of detection. Densitometry measurements are performed by placing the light source, which for these embodiments can be a white light source, underneath the sample tray. The sample tray can be of a transparent material such as glass or fused silica. One example of a white light source is a white LED array; another is a fluorescent white light. Alternatives to a white light source are a UV light source and light sources emitting light at any of the wavelengths mentioned above. For densitometry measurements, the light source is enclosed and light from the source passes from the enclosure through a slit that is positioned across and underneath the sample tray, and oriented in a direction transverse to the direction of travel of the sample tray. In a manner analogous to the fluorescence embodiments described above, the sample tray travels in a linear direction at a precisely controlled rate, and the light that is not absorbed and is within the field of the lens is collected by the lens and imaged onto the detector. An emission filter can also be included.

Instruments in accordance with this invention can also be constructed to perform area CCD imaging for samples that are detected by way of chemiluminescence emission, in addition to the instrument's capability for scanning with a line of light and time delay integration of the signal. To perform area imaging, which is also referred to as operating in a "full-frame" mode or obtaining a "full-frame" image, the stage with the sample tray is centered relative to the camera, and the image of the chemiluminescence pattern from the sample is collected by the full area of the CCD and processed accordingly, without illumination of the sample by a light source. Since an emission filter is not needed in this imaging mode, the filter wheel can have a position that has a clear opening without any filter, to allow the emission light to focus on the CCD as needed. The same CCD camera can thus be used both in a moving line mode and a full-frame mode at the selection of the operator. The instrument software can itself be programmed to offer the user a choice between the moving line mode and the full-frame mode. The moving line mode will generally be used for imaging samples that are not chemiluminescent.

A single instrument can thus be used to present a choice among multiple imaging platforms such as fluorescence, colorimetry, chemiluminescence, and densitometry, as well as a choice between operating in a moving-line mode and a full-frame mode. Instruments designed to choose between epi-illumination and trans-illumination, or to perform both simultaneously or in succession, are also within the scope of this invention. A single instrument can thus produce fluorometric or calorimetric analyses by epi-illumination and fluorometric or densitometric analyses by trans-illumination.

Processing of the data collected by the CCD and other instrument functions such as selection and control of the light sources are readily performed by computer 33 (FIG. 1) using conventional software used in biotechnology laboratories and known in the art. As noted above, the software can govern the movement of the moving parts of the system and coordinate the moving parts with the time delay integration of the CCD. When multiple scans are performed at different wavelengths, software can be used that overlays and aligns the scans to form a single superimposed image.

Another way to utilize the apparatus and method of this invention is to first perform a pre-scan to obtain an estimate of the intensities of the signals that are being emitted by the sample. Once these estimates are obtained, operating conditions can be selected that will be optimal for producing an image of the sample. The scan is then repeated with the instrument set at these optimal conditions. The operating conditions may include the relative speed of movement between the sample and the detector, the intensity of the light source(s), and the start and stop timing of data collected by the detector. The determination of the optimal conditions can be accomplished by automated instrumentation. A pre-scan can also be used to locate an area or areas of interest within a sample area, such as areas emitting signals of high intensity relative to adjacent areas, and then performing a second scan on the area(s) of interest only.

The apparatus and method of this invention are useful in the imaging of a single two-dimensional sample on a sample tray, as well as in the imaging of a series of samples. The sample stage 11 can thus be replaced with a moving endless surface such as a conveyor belt on which a large number of samples can be placed. This allows a multitude of samples to be imaged at a high throughput rate, and is particularly susceptible to automation. Samples of varying lengths can also be processed in this manner.

While the foregoing description describes various alternatives to the components shown in the Figures, still further alternatives will be apparent to those who are skilled in the art and are within the scope of the invention. For example, an apodizing filter can be interposed in the excitation path to enhance the uniformity of the line of light. An apodizing filter can also be interposed in the detection path to compensate for lens distortions in the detector and thereby improve the uniformity of the light collected by the CCD.

Further disclosures of potential relevance to the invention are found in the following:

Oldham et al., United States Patent Application Publication No. US 2005/0036142 A1, published Feb. 17, 2005. Like the Applera Corporation document cited above, this patent application describes a system for use on samples held in capillaries or channels, and operates by simultaneously illuminating an area of the sample with multiple illumination wavelengths and capturing the emitted signals with an area detector in time delay integration mode.

Brown et al., United States Patent Application Publication No. US 2003/0048933 A1, published Mar. 13, 2003, discloses a system for inspecting microarrays that uses time delay integration.

McKean et al., U.S. Pat. No. 4,960,999, issued Oct. 2, 1990, discloses a system in which a UV light source illuminates a narrow portion of a moving gel, and the emitted light from the gel is collected through a synchronized scanning aperture onto a CCD camera whose position is adjustable.

In the claims appended hereto, the term "a" or "an" is intended to mean "one or more." The term "comprise" and variations thereof such as "comprises" and "comprising," when preceding the recitation of a step or an element, are intended to mean that the addition of further steps or elements is optional and not excluded. All patents, patent applications, and other published reference materials cited in this specification are hereby incorporated herein by reference in their entirety. Any discrepancy between any reference material cited herein and an explicit teaching of this specification is intended to be resolved in favor of the teaching in this specification. This includes any discrepancy between an art-understood definition of a word or phrase and a definition explicitly provided in this specification of the same word or phrase.

What is claimed is:

1. Apparatus for forming a two-dimensional image of a two-dimensional sample array, said apparatus comprising:
   a sample holder defining a planar sample area having a width and a length;
   a light source forming a line of light that spans said width of said sample area;
   means for moving either said sample holder or said light source along an axis parallel to said length of said sample holder to thereby expose said entire sample area to said line of light;
   a detector comprising a CCD camera in time delay integration mode, said detector arranged to collect light emerging from said sample area as said sample area is illuminated by said line of light; and
   means for computerized processing of data collected by said detector to assemble an image of said sample area as said means for moving exposes said entire sample area to said line of light.

2. The apparatus of claim 1 wherein said light source and said detector are on the same side of said sample holder, thereby producing epi-illumination.

3. The apparatus of claim 1 wherein said light source and said detector are on opposite sides of said sample holder, thereby producing trans-illumination.

4. The apparatus of claim 1 wherein said light source is a linear array of LEDs.

5. The apparatus of claim 4 wherein said linear array of LEDs is coupled with an interference band pass filter.

6. The apparatus of claim 1 wherein said light source is a laser light source projected as a line of light.

7. The apparatus of claim 1 further comprising means for selecting among a plurality of light sources of different wavelengths.

8. The apparatus of claim 7 wherein said means for selecting among a plurality of light sources of different wavelengths utilizes band pass filters.

9. The apparatus of claim 1 wherein said detector further comprises means for collecting fluorescence emissions at a plurality of emission wavelength bands by use of optical filters, and said means for computerized processing of data comprises means for overlaying and aligning data obtained in a plurality of scans, each scan collecting light at one of said plurality of wavelength bands.

10. The apparatus of claim 1 further comprising an apodizing filter arranged between said light source and said sample holder to improve uniformity of light along the length of said line of light.

11. The apparatus of claim 1 wherein said means for moving causes said sample holder to move while said light source remains stationary.

12. The apparatus of claim 1 wherein said means for moving causes said light source to move while said sample holder remains stationary.

13. The apparatus of claim 1 wherein said means for computerized processing comprises means for selecting between (i) assembling a full-frame chemiluminescence image of said sample area without illumination of said sample area by said light source and (ii) assembling an image of said sample area other than by chemiluminescence as said means for moving exposes said entire sample area to said line of light.

14. A method for forming a two-dimensional image of a two-dimensional sample array, said method comprising:
   (a) placing said sample array on a planar sample area having a length and width in an apparatus that comprises (i) a sample holder having a surface that includes said sample area, (ii) a light source forming a line of light that spans said width of said sample area, and (iii) a detector comprising a CCD camera in time delay integration mode arranged to collect light emerging from said sample area as said sample area is illuminated by said line of light;
   (b) moving either said sample holder or said light source along an axis parallel to said length of said sample holder to expose said entire sample area to said line of light; and
   (c) processing data collected by said detector to assemble a two-dimensional image of said sample array.

15. The method of claim 14 wherein said light source and said detector are on the same side of said sample holder, thereby producing epi-illumination.

16. The method of claim 14 wherein said light source and said detector are on opposite sides of said sample holder, thereby producing trans-illumination.

17. The method of claim 14 wherein said light source is a laser light source projected as a line of light.

18. The method of claim 14 wherein said apparatus comprises a first light source on the same side of said sample holder as said detector to produce epi-illumination, and a second light source on the opposite side of said sample holder as said detector to provide trans-illumination, said method comprising performing either or both of (1) fluorometric detection, colorimetric analysis, or both fluorometric and calorimetric detection by said epi-illumination and (2) either fluorometric or densitometric detection by trans-illumination.

19. The method of claim 14 wherein said light source is a linear array of LEDs.

20. The method of claim 14 wherein said light source is a laser light source projected as a line of light.

21. The method of claim 14 further comprising collecting light by a plurality of scans, each scan performed at a different emission wavelength band by use of optical filters, and overlaying and aligning data obtained in said plurality of scans.

22. The method of claim 14 wherein (b) comprises moving said sample holder while maintaining said light source stationary.

23. The method of claim 14 wherein (b) comprises moving said light source while maintaining said sample holder stationary.

24. The method of claim 14 wherein said sample array is a phosphor screen.

25. The method of claim 14 further comprising first performing steps (a), (b), and (c) to determine optimal operating parameters for assembling said two-dimensional image of said sample array, and then repeating steps (a), (b), and (c) under optimal operating parameters so determined to assemble said two-dimensional image.

26. The method of claim 14 further comprising first performing steps (a), (b), and (c) to locate an area of interest in said sample array as defined by a higher signal emitted from said area of interest than from adjacent areas, and then repeating steps (a), (b), and (c) while limiting said steps to said area of interest.

* * * * *